United States Patent
Rust et al.

(10) Patent No.: US 10,991,149 B2
(45) Date of Patent: Apr. 27, 2021

(54) EMBEDDED VIRTUAL LIGHT SOURCE IN 3D VOLUME LINKED TO MPR VIEW CROSSHAIRS

(71) Applicant: KONINKLIJKE PHILIPS N.V., Eindhoven (NL)

(72) Inventors: David Rust, Seattle, WA (US); Dorothy Anita Strassner, Redmond, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/498,446

(22) PCT Filed: Mar. 29, 2018

(86) PCT No.: PCT/EP2018/058155
§ 371 (c)(1),
(2) Date: Sep. 27, 2019

(87) PCT Pub. No.: WO2018/178274
PCT Pub. Date: Oct. 4, 2018

(65) Prior Publication Data
US 2020/0105048 A1    Apr. 2, 2020

Related U.S. Application Data

(60) Provisional application No. 62/478,058, filed on Mar. 29, 2017.

(51) Int. Cl.
*G06T 15/08* (2011.01)
*A61B 8/00* (2006.01)
*A61B 8/08* (2006.01)
*G06T 15/50* (2011.01)
(Continued)

(52) U.S. Cl.
CPC .............. *G06T 15/08* (2013.01); *A61B 8/466* (2013.01); *A61B 8/483* (2013.01); *A61B 8/5253* (2013.01);
(Continued)

(58) Field of Classification Search
CPC ....... A61B 8/466; A61B 8/483; A61B 8/5253; G06T 15/00–87; G06T 7/0014;
(Continued)

(56) References Cited

U.S. PATENT DOCUMENTS

| | | | |
|---|---|---|---|
| 6,342,887 B1 * | 1/2002 | Munroe | G06T 15/50 345/419 |
| 2004/0075658 A1 | 4/2004 | Goto | |

(Continued)

FOREIGN PATENT DOCUMENTS

| | | |
|---|---|---|
| EP | 1659513 A2 | 5/2006 |
| JP | 2000090283 A | 3/2000 |
| WO | 2004095378 A1 | 11/2004 |

OTHER PUBLICATIONS

International Search Report for International Application Serial No. PCT/EP2018/058155, filed Mar. 29, 2018, 4 pages.
(Continued)

*Primary Examiner* — Daniel F Hajnik (57) ABSTRACT

An ultrasonic diagnostic imaging system has an array probe for acquiring a 3D image dataset of a subject. Volume rendering is performed to produce a volume image of the subject, and MPR reconstruction is performed to produce three orthogonal 2D images of the subject. The point of intersection of the three 2D image planes is locationally marked by a crosshair or other graphic in each 2D image. The corresponding location in the volume image is marked with a virtual light source which illuminates the interior of the 3D volume and is positionally linked to the location markers in the MPR images.

10 Claims, 4 Drawing Sheets

(51) Int. Cl.
*G06T 19/00* (2011.01)
*G06T 7/00* (2017.01)

(52) U.S. Cl.
CPC .......... *G06T 7/0014* (2013.01); *G06T 15/506* (2013.01); *G06T 19/00* (2013.01); *G06T 19/003* (2013.01); *G06T 2207/10136* (2013.01); *G06T 2210/41* (2013.01)

(58) Field of Classification Search
CPC ....... G06T 2207/10136; G06T 2210/41; G06T 15/08; G06T 15/506; G06T 19/00; G06T 19/003
See application file for complete search history.

(56) References Cited

U.S. PATENT DOCUMENTS

| | | |
|---|---|---|
| 2009/0002366 A1 | 1/2009 | Kanitsar et al. |
| 2010/0328305 A1 | 12/2010 | Vining |
| 2012/0245465 A1 | 9/2012 | Hansegard et al. |
| 2013/0195313 A1* | 8/2013 | Gauthier .............. A61B 8/0833 382/103 |
| 2014/0205168 A1* | 7/2014 | Kim ....................... G06T 15/08 382/131 |
| 2014/0232719 A1 | 8/2014 | Wahrenberg |
| 2015/0042657 A1* | 2/2015 | Smith-Casem ......... G06T 15/08 345/427 |
| 2016/0030007 A1 | 2/2016 | Tsujita |
| 2016/0292913 A1 | 10/2016 | Wahrenberg |
| 2017/0365051 A1* | 12/2017 | Wahrenberg ............ G06T 15/50 |

OTHER PUBLICATIONS

Kohlmann, et al., "LiveSync: Smart Linking of 2D and 3D Views in Medical Applications", PhD-Thesis, Dec. 17, 2008, pp. 1-5.

* cited by examiner

EMBEDDED VIRTUAL LIGHT SOURCE IN 3D VOLUME LINKED TO MPR VIEW CROSSHAIRS

RELATED APPLICATIONS

This application is the U.S. National Phase application under 35 U.S.C. § 371 of International Application No. PCT/EP2018/058155, filed on Mar. 29, 2018, which claims the benefit of Provisional Application Ser. No. 62/478,058, filed Mar. 29, 2017. These applications are hereby incorporated by reference herein.

This invention relates to three-dimensional ultrasonic imaging and, in particular, to the linking of MPR view crosshairs to an embedded virtual light source location marker in a corresponding three-dimensional ultrasound image.

For over forty years, diagnostic ultrasonic imaging has been dominated by two-dimensional (2D) imaging. Starting with B-arm systems, then mechanically oscillated transducers, and finally electronically steered beam array probes, ultrasonic imaging has evolved from static 2D imaging to high quality real time imaging. Sonographers thus became accustomed to navigating through the body with 2D images and recognizing pathology for diagnosis in 2D images. About fifteen years ago ultrasound took another step forward in evolution with real time phased three-dimensional (3D) imaging. While 3D images of anatomy provide more diagnostic information that 2D images, they were nonetheless unfamiliar to many sonographers, who were used to seeing only 2D views of anatomy. Despite continuing adoption of 3D ultrasound technology, 3D navigation of ultrasound volume images continues to be difficult for many sonographers and physicians even though 3D capabilities have been on the market for many years. To assist clinicians with 3D volume navigation, a viewing format was developed which presented the 3D image data in both 3D and more familiar 2D images. In addition to displaying the 3D volume image, the ultrasound system would also display three 2D images of intersecting (usually orthogonal) planes in the 3D volume. Thus, if the clinician spotted anatomy in the 3D volume image that seemed unfamiliar, he or she could position one or more of the 2D image planes to intersect the anatomy of interest and visualize it in a more familiar 2D view. Since the three 2D planes would all intersect at one point in the image volume, the clinician could position this intersection point on a target in the 3D volume, thereby visualizing target anatomy in three different cut plane views. But despite widespread use of this combined 2D-3D visualization technique, 3D image navigation remains challenging for many clinicians. One issue in particular is referencing a point identified in one of the 2D images to a location in the 3D volume presentation. Accordingly, it is desirable to provide imaging tools which further aid the clinician in navigating 3D volume images.

In accordance with the principles of the present invention, an ultrasonic diagnostic imaging system and display technique are described in which an image display comprises a 3D volume image and one or more intersecting 2D planar image views of the image volume. A location marker or crosshair is present in each 2D image corresponding to the same point in space and is also present at the same point in space in the volume image. The location marker in the volume image is not a crosshair, however, but is a virtual light source spatially linked to the location markers or crosshairs of the 2D images. The location markers or crosshairs and the virtual light source can be repositioned, and are spatially linked so that repositioning a location marker or crosshair in a 2D image will cause a corresponding repositioning of the virtual light source in the volume image, and/or vice versa.

Figure 1:
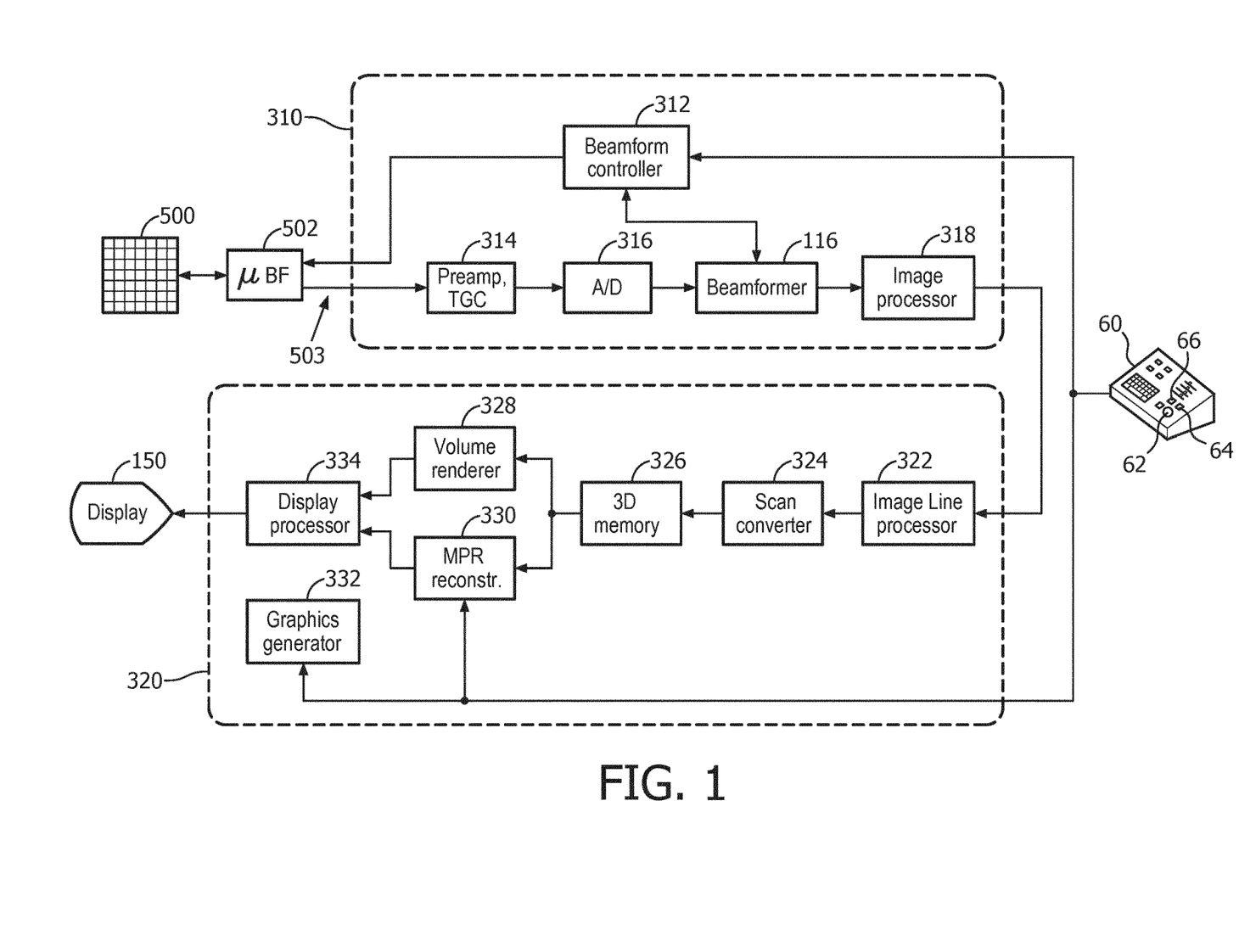
FIG. 1 illustrates in block diagram form an ultrasound system constructed in accordance with the principles of the present invention.

Referring first to FIG. 1, an ultrasound system constructed in accordance with the principles of the present invention is shown in block diagram form. In this implementation an ultrasound probe includes a two-dimensional array transducer 500 and a microbeamformer 502. The microbeamformer contains circuitry which control the signals applied to groups of elements ("patches") of the array transducer 500 and does some processing of the echo signals received by elements of each group to produce partially beamformed signals. Microbeamforming in the probe advantageously reduces the number of conductors in the cable 503 between the probe and the ultrasound system and is described in U.S. Pat. No. 5,997,479 (Savord et al.) and in U.S. Pat. No. 6,436,048 (Pesque).

The probe is coupled to the scanner subsystem 310 of the ultrasound system. The scanner includes a beamformer controller 312 which is responsive to a user control 60 and provides control signals to the microbeamformer 502 instructing the probe as to the timing, frequency, direction and focusing of transmit beams. The beamformer controller also controls the beamforming of received echo signals by its coupling to analog-to-digital (A/D) converters 316 and a beamformer 116. Echo signals received by the probe are amplified by preamplifier and TGC (time gain control) circuitry 314 in the scanner, then digitized by the A/D converters 316. The digitized echo signals are then formed into fully coherent beams by a beamformer 116. The echo signals are processed by a signal processor 318 which performs digital filtering, B mode detection, and Doppler processing, and can also perform other signal processing functions such as harmonic separation, speckle reduction through frequency or spatial compounding, and other desired image processing.

The echo signals produced by the scanner subsystem 310 are coupled to the digital display subsystem 320, which processes the echo signals for display in the desired image format. The echo signals are processed by an image line processor 322, which samples the echo signals, splices segments of beams into complete line signals, and averages line signals for signal-to-noise improvement or flow persistence. The image lines are scan converted into the desired image format by a scan converter 324 which performs R-theta to Cartesian coordinate conversion as is known in the art. The scan converter also fills in image areas between received echo signals and beams by interpolation. Individual image pixel values from each beam are stored in a 3D memory 326 which are addressable in accordance with their x, y, and z coordinate locations in a 3D volume being scanned. The final images produced from the 3D image data stored in the 3D memory are overlayed with graphics to be displayed with the image. These graphics are generated by a graphics generator 332 which is responsive to the user control for the input and display of patient identifying information or the movement of cursors, for example, or location markers in the form of crosshair graphics as described below.

Figure 2:
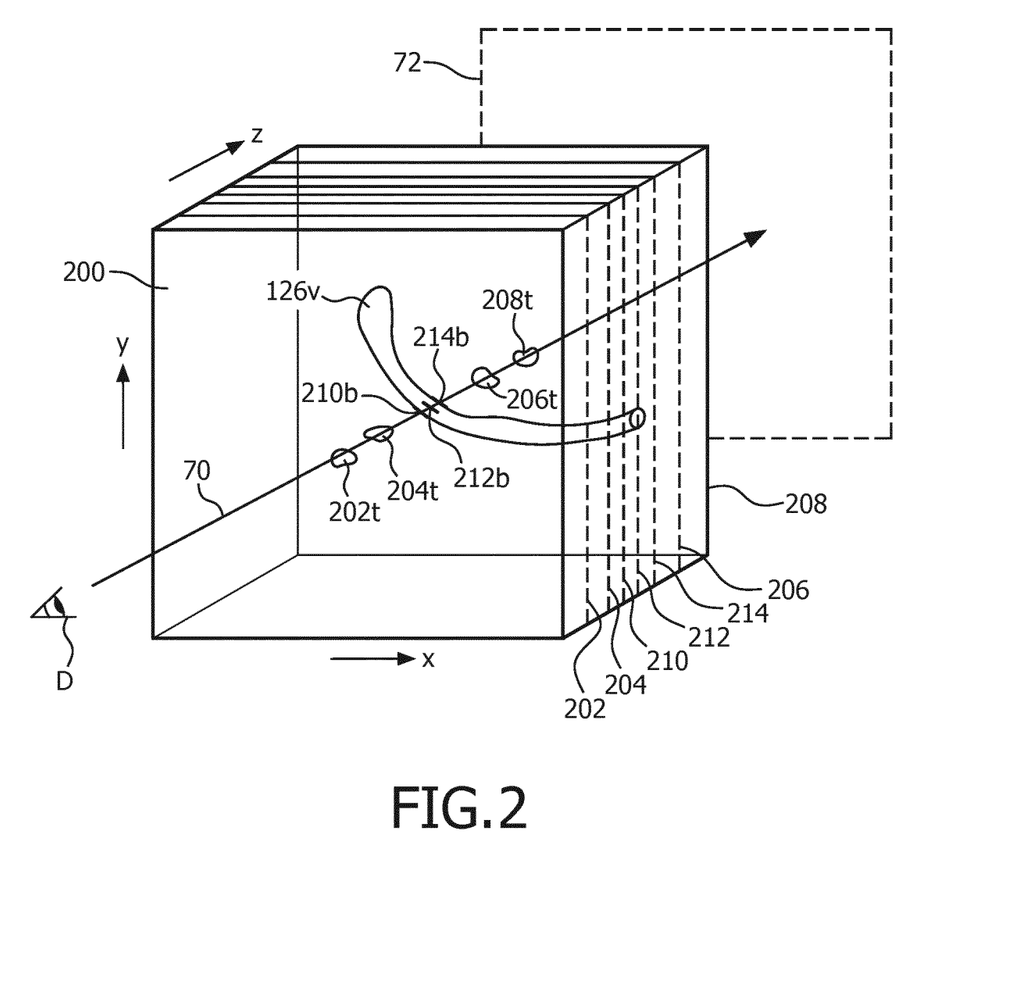
FIG. 2 is an illustration of the rendering process performed by the volume renderer of FIG. 1.

For real-time volumetric imaging the display subsystem 320 also includes a volume renderer 328 which receives a 3D data set or a set of spatially separated 2D images from the 3D memory and renders them into a real-time three-dimensional image. Volume rendering from 3D image datasets is well known and functions to convert a particular view of a scanned 3D object to a 2D image view suitable for display on a two-dimensional viewing medium such as a computer monitor. The volume rendering process is illustrated in FIG. 2. A block 200 represents the image data stored in the 3D memory 326 and addressable in x, y, and z coordinates, here arranged spatially as a block of image data of scanned image planes. In this example the image data was acquired by scanning successive planes with the array transducer 500: image plane 202, image plane 204, and so on. The image planes of x, y image data are shown stacked in the z dimension in the drawing, thus providing the z coordinate for the data. Volume rendering is performed by ray casting, the projection of many parallel virtual lines 70 through the volume 200 in a particular viewing direction of the volume by a viewer D. The pixels encountered along a virtual line 70 are accumulated in accordance with a desired rendering algorithm (e.g., surface rendering, maximum value rendering, mean value rendering) to produce one pixel value for a 2D image rendered in projection plane 72. In the example of FIG. 2, virtual projection line 70 intersects tissue pixels t and blood pixels b as it passes through the anatomical image dataset of block 200. The line 70 is seen to intersect a tissue pixel 202t on plane 202, then tissue pixel 204t on plane 204. The line 70 then intersects three blood pixels, 210b, 212b, and 214b of blood vessel 126v on planes 210, 212, and 214, respectively. Then the projection line intersects tissue pixels 206t and 208t on planed 206 and 208. The intersected pixel values are processed in accordance with the selected rendering algorithm. When the process is repeated for sufficient virtual projection lines necessary to produce a desired image pixel density for the rendered image, the result is a 2D image in x and y of the volume as seen from the particular viewing direction. The rendering algorithm can be described in general as $$P_{x,y}(\theta) = \sum_{i=1}^{N} f(P_1 \ldots P_{i-1}) P_i$$

where $P_{x,y}(\theta)$ is an image point at x,y coordinate in projection plane 72 when the volume 200 is viewed at angle $\theta$ to the 3D dataset, and N are the data values encountered along a projection line. The function $f(P_1 \ldots P_{i-1})$ is the desired rendering function such as an opacity-transparency function used to view tissue as opaque and fluid as transparent or vice versa as described in U.S. Pat. No. 5,720,291 (Schwartz). In the implementation of the present invention described below, the rendering function includes an illumination factor which is a function of the distance from a virtual light source to the points along the virtual line 70. A maximum intensity projection can be produced by rendering the 3D dataset in accordance with the expression $$P_{x,y}(\theta) = \underset{i=1,N}{\mathrm{Max}}[P_i]$$

and a mean intensity projection can be produced by rendering the dataset in accordance with the expression $$P_{x,y}(\theta) = \left(\frac{1}{N}\right) \sum_{i=1}^{N} P_i$$

A plurality of such projection images can be formed from a given 3D dataset, each at a slightly different viewing direction $\theta$, then replayed in real time succession to present a moving view of the 3D volume while rotating, a presentation technique known as dynamic parallax. Further details on volume rendering may be found in Kaufman, A., *Introduction to Volume Visualization*, IEEE Computer Society Press, 1991.

Figure 3:
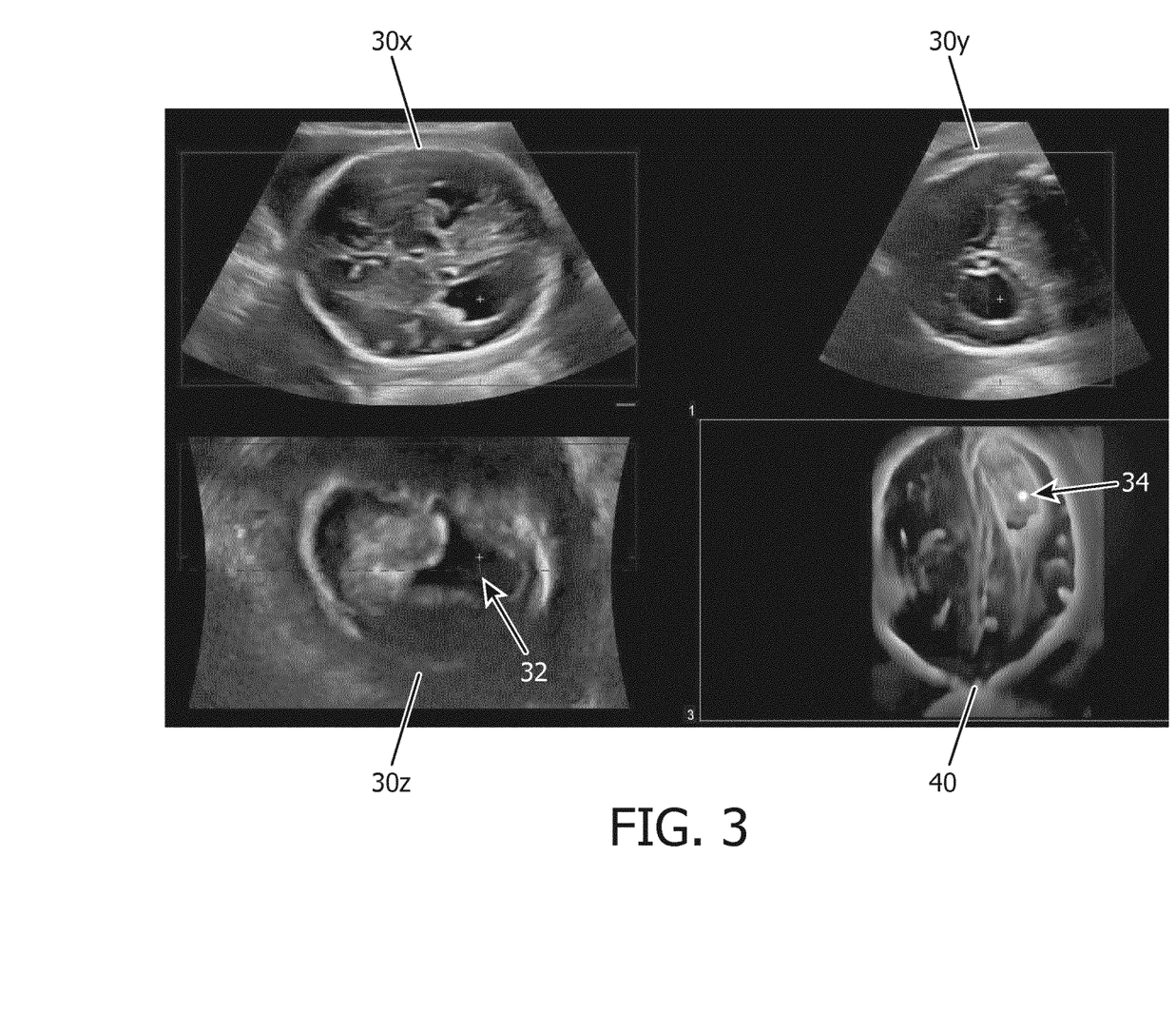
FIG. 3 illustrates three 2D planar images and a corresponding 3D volume image with crosshairs in the planar images positionally linked to a virtual light source location marker in the 3D volume image.

The ultrasound system of FIG. 1 includes another processor which operates on the 3D image data, an MPR reconstruction circuit 330. The MPR (multiplanar reconstruction) circuit selects pixel values in a desired plane through the 3D data set and produces a 2D image from pixels located in the plane. Once a user selects a plane through the volume data, the x, y, z addresses of every point in the volume of data which intersects the plane can be calculated geometrically. In principle the plane can be at any inclination through the volume dataset, but a preferable set of MPR images for an implementation of the present invention is a set of three orthogonal planes, one with data points in y, z with a constant x value, another with data points in x, z with a constant y value, and a third with data points in x, y with a constant z value. Non-orthogonal intersecting planes may also be employed. Three such intersecting planes will intersect at one point in 3D space, a point which is also present in a 3D volume image produced by volume renderer 328. A display processor 334 arranges the images in the desired display format such as adjacent to each other as shown in FIG. 3, and overlays any display graphics produced by the graphics generator, also illustrated in FIG. 3. The formatted image display is then displayed on the screen of display 150.

A user interface 60 includes controls 62-66 for control of the orientation of the volumetric region scanned by the two-dimensional array probe and manipulation of the MPR planes. The user can select a function to be controlled by means of a control 66, such as the orientation of the region in front of the probe to be scanned. The user then uses a joystick or trackball 62 to position the scanned region. Once the scanned region has been set, the user depresses a control 64 to lock in the setting. The beamformer controller 312, the beamformer 116, and the microbeamformer 502 respond to these setting changes by transmitting beams in a desired direction by phased transmission with elements of the two-dimensional array 500, then steering received beams in the same directions to acquire a series of receive beams throughout the volumetric region being scanned. These receive beams are processed into scan lines of image values in 3D space, then rendered into a 3D image of the scanned volume by volume rendering. Two dimensional MPR images are formed of one or more cut planes through the 3D volume by MPR reconstruction. The display screen shows a rendered volume image and one or more (preferably three) planar MPR images of the scanned volume.

As mentioned above, a preferred implementation of the present invention displays three mutually intersecting MPR images and a 3D volume image, all of the same volumetric region. The three MPR images intersect at a common point, and the positions of the planes of the MPR images can be adjusted by a user control 60 so that the common intersection point is in a region of interest. To aid in making this adjustment, the common intersection point is marked in each MPR image by a location marker, such as the "+" crosshair 32 illustrated in the MPR images 30x, 30y, and 30z of FIG. 3. The + crosshair displayed over each image is produced by the graphic generator 332, which is coupled to the control panel 60 by which the plane repositioning is manipulated. Thus, when orthogonal planes are used, a clinician can see a target anatomy in an x-plane, a y-plane, and a z-plane and can reposition the planes until the crosshair + in each image is positioned over the target anatomy. The same intersection point location can be marked in the volume by a similar crosshair marker +, which can be produced automatically from the x, y, z coordinates of the plane intersection point.

Figure 4A:
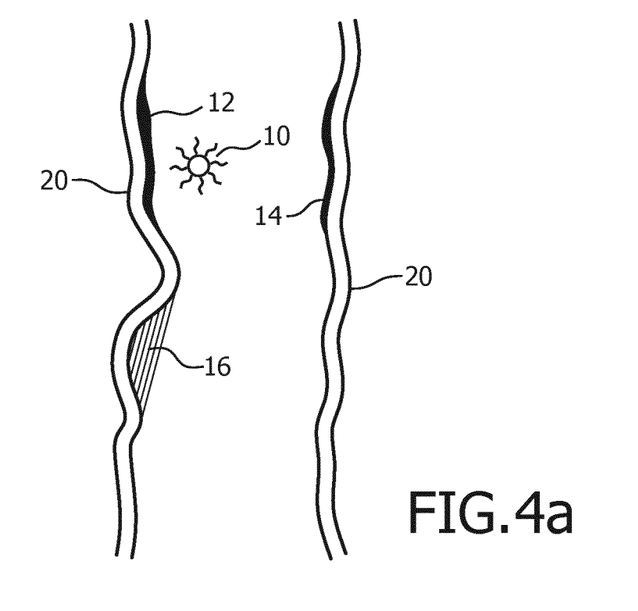
FIGS. 4a and 4b illustrate the effects of change of anatomical illumination caused by a change in position of a virtual light source in a 3D volume image.
Figure 4B:
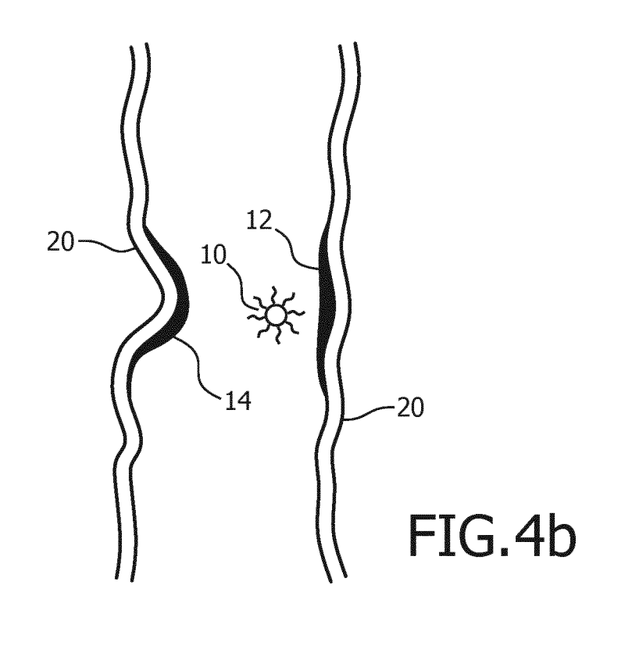

However, a clinician unfamiliar with 3D imaging and plane manipulation may find it difficult to perceive the intersection point in space in the 3D image, thus making it difficult to manipulate the images. In accordance with the present invention, the plane intersection point in the volume image is displayed, not as a crosshair +, but as a virtual light source orb, shown as a white light orb and indicated by arrow 34 in the volume image 40 of FIG. 3. The use of virtual light sources in ultrasound images for virtual colonoscopy is described in US pat. pub. no. 2016/0292913 (Wahrenberg), for instance. The virtual light source in the image 40 is produced by the graphics generator as an icon which overlays the volume image, in this example a white light orb. Other colors may also be used. It is also seen in the volume image 40 that the virtual light source is illuminating the surrounding walls of the cavity in which it is located. This lighting and shadowing enhance the 3D image, providing visual cues that better enable a clinician to perceive the anatomy in which the virtual light source is located and thereby aids in MPR plane position adjustment. The volume image 40 is produced by surface rendering, which renders fluid as transparent and tissue surfaces as solid surfaces. In FIG. 4, the virtual light source 34 is located in a fluid-filled cavity of a subject and is illuminating the walls of the cavity. This illumination effect of the surfaces of the cavity is produced during the volume rendering process by combining an illumination factor with each pixel which represents part of the wall of the cavity illuminated by the light source. To provide a realistic illumination effect, the illumination factor used for a wall pixel should decline with distance of that pixel from the virtual light source. In nature, the intensity of light produced by a light source falls off as a function of the inverse square law applied to the distance. Thus, an implementation of the present invention can operate by determining when a pixel produced by surface rendering computation along a projection line 70 is a surface pixel of the cavity in which a virtual light source is located. The pixel is an illuminated surface pixel of the cavity if there are no tissue pixels along a line between the surface pixel and the location of the virtual light source. For instance, if all of the pixels between a surface pixel and the virtual light source location are blood pixels, then the surface pixel is an illuminated wall pixel of the cavity in which the virtual light source is located. Once this analysis has found that the pixel is an illuminated wall pixel of the cavity, then its color or display brightness or intensity is adjusted to reflect illumination by the light source. One appropriate illumination factor which can be used is calculated by applying the inverse square law to the distance between the cavity wall pixel location and the virtual light source location, the distance along the virtual line previously used to determine if the pixel was an illuminated cavity wall pixel (only intervening fluid). For example, a cavity wall pixel of a point 5 mm from the light source will have its brightness increased by one illumination factor, and another wall pixel 3 mm from the light source will have its brightness increased by a greater illumination factor. A wall pixel which is shadowed from the virtual light source will not have its brightness increased at all. Thus, the closer a portion of the cavity wall is to the virtual light source, the greater its brightness. The same effect can be produced using color hues or intensities.

This illumination effect may be better appreciated by referring to FIG. 4, which represents a blood vessel in two-dimensional cross-section, having vessel walls 20. In FIG. 4a a virtual light source 10 is positioned near the top of the vessel and close to the left wall of the vessel. The light source will thus more brightly illuminate the vessel wall on the left, indicated by surface 12 along the left wall, than it will illuminate the right vessel wall as indicated by surface 14. It is also seen that there is a bend of the left vessel wall 20 below the light source 10. This bend causes the portion of the vessel wall below the bend to be shadowed from the light source, as indicated by the shadowed region 16. Thus there are three types of wall surface illumination in this example, a brightly illuminated vessel wall 12, a less brightly illuminated vessel wall 14, and a shadowed vessel wall 16 which, absent a light scattering effect, is not illuminated at all by the light source.

In FIG. 4b the virtual light source 10 is positioned lower in the vessel and closer to the right vessel wall 20. The area 12 of the wall surface will be most brightly illuminated by reason of the short distance between the light source and the right vessel wall. The left vessel wall is also illuminated by the light source as indicated at 14, but less brightly by reason of the greater distance from the light source to the left wall. With the light source in the illustrated position there is no shadowing of any section of vessel wall, and so an illumination factor can be added or applied to the brightness, hue or intensity of every pixel along the vessel walls, as a function of the inverse square law of the distance to the light source or by some other (e.g., linear) declining illumination factor.

An implementation of the present invention thus uses a virtual light source as a location marker in the volume image, with the light source marking a corresponding location in one or more 2D images, such as the intersection point of MPR images of three orthogonal planes through the imaged volume. The intersection point is marked in the MPR images also, as by crosshairs as indicated at 32 in FIG. 3 or by dashed lines drawn horizontally and vertically over each 2D image which represent the positions of the other intersecting image planes. Other markers may also be employed. The markers in the 2D images are operationally linked to the virtual light source marker 34 in the volume image; as one of the 2D image planes is repositioned, the virtual light source is automatically repositioned in the volume image in correspondence with the change in the plane intersection point, and/or vice versa.

It should be noted that an ultrasound system which performs 3D imaging such as that shown in FIG. 1 may be implemented in hardware, software or a combination thereof. The various embodiments and/or components of an ultrasound system, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system. The computer or processor may also include a memory. The memory devices such as the A-line memory 24 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including the shear wave measurement and background motion compensation subsystem described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. For example, the equations calculated by the volume renderer and the MPR reconstruction circuit may be executed by software modules calculating the equations. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasonic diagnostic imaging system for three dimensional (3D) imaging, comprising:
   an ultrasound probe comprising an array transducer adapted to scan a subject in three dimensions;
   a 3D image data memory, coupled to the ultrasound probe, and adapted to store a 3D image dataset of the subject;
   a volume renderer, coupled to the image data memory, and adapted to render a volume image of the subject and an illumination effect of a virtual light source within the rendered volume image;
   a 2D image reconstruction circuit, coupled to the image data memory, and adapted to produce a plurality of 2D images of intersecting planes of the subject, wherein the 2D images further comprise graphic markers of a point of intersection of the 2D image planes;
   a graphics generator adapted to produce image graphics; and
   a display adapted to simultaneously display a volume image and one or more 2D images of the subject with image graphics, and
   wherein the volume image comprises the virtual light source which is displayed positionally located within the volume image to mark the point of intersection of the 2D image planes within the subject and is operationally linked to the current point of intersection of the 2D image planes,
   wherein the location of the virtual light source within the volume image is adapted to change with change in the point of intersection of the 2D image planes, and
   wherein a change in the point of intersection of the 2D image planes is adapted to result in a change in the illumination effect within the rendered volume image.

2. The ultrasonic diagnostic imaging system of claim 1, wherein volume image is further displayed with a virtual light source graphic produced by the graphics generator.

3. The ultrasonic diagnostic imaging system of claim 1, wherein the effect of illumination is adapted to produce a greater illumination of structure closer to the virtual light source and a lesser illumination of structure farther from the virtual light source.

4. The ultrasonic diagnostic imaging system of claim 3, wherein the greater illumination and the lesser illumination are a function of the inverse square law with respect to distance to the virtual light source.

5. The ultrasonic diagnostic imaging system of claim 3, wherein the effect of illumination is produced as a difference in brightness, hue, or intensity.

6. The ultrasonic diagnostic imaging system of claim 1, wherein the volume image displayed with the virtual light source and the one or more 2D images are adapted to be displayed concurrently.

7. The ultrasonic diagnostic imaging system of claim 1, wherein the 2D image reconstruction circuit further comprises a multiplanar image reconstruction circuit.

8. The ultrasonic diagnostic imaging system of claim 7, wherein the multiplanar image reconstruction circuit is further adapted to produce three 2D images of intersecting planes of the subject.

9. A method for displaying three dimensional ultrasonic image data of a subject comprising:
   displaying a volume rendering of the ultrasonic image data and the effect of illumination produced by a virtual light source within the rendered volume;
   displaying concurrently a plurality of 2D images of planes of the ultrasonic image data;
   displaying in each of the 2D images a location marker of a point of intersection of the planes of the images;
   positioning in the volume rendering the virtual light source;
   displaying the volume rendering with the virtual light source displayed as a marker of the point of intersection of the planes of the 2D images in the volume rendering; and wherein the location of the virtual light source in the volume rendering is operationally linked to the location markers of the current point of intersection of the 2D images so as to change with change in the point of intersection of the 2D image planes, and wherein a change in the point of intersection of the 2D image planes results in a change in the effect of illumination within the rendered volume.

10. The method of claim 9, wherein displaying concurrently further comprises displaying concurrently three 2D images of mutually orthogonal image planes; and wherein displaying the volume rendering with the effect of illumination further comprises displaying an effect of illumination which falls off as a function of the inverse square of distance to the virtual light source.

* * * * *